US005532128A

United States Patent [19]

Eggers et al.

[11] Patent Number: 5,532,128
[45] Date of Patent: Jul. 2, 1996

[54] MULTI-SITE DETECTION APPARATUS

[75] Inventors: Mitchell D. Eggers; Michael E. Hogan; Kenneth L. Beattie, all of The Woodlands; John Shumaker, Houston, all of Tex.; Daniel J. Ehrlich, Lexington; Mark Hollis, Concord, both of Mass.

[73] Assignee: Houston Advanced Research Center, The Woodlands, Tex.

[21] Appl. No.: 353,957

[22] Filed: Dec. 12, 1994

Related U.S. Application Data

[63] Continuation of Ser. No. 794,036, Nov. 19, 1991, abandoned.

[51] Int. Cl.⁶ .......................... G01N 33/543; G01N 27/22
[52] U.S. Cl. .......................... 435/16; 204/400; 204/403; 422/82.01; 422/82.02; 435/7.1; 435/7.2; 435/287.1; 435/287.2; 436/518; 436/524; 436/525; 436/527; 436/806; 436/809
[58] Field of Search ........................ 204/153.1, 153.12, 204/400, 403; 422/82.01, 82.02; 435/6, 7.1, 7.2, 287, 291, 287.1, 287.2; 436/518, 524, 525, 527, 806, 809

[56] References Cited

U.S. PATENT DOCUMENTS

| | | | |
|---|---|---|---|
| 4,072,576 | 2/1978 | Arwin et al. | 436/806 |
| 4,098,645 | 7/1978 | Hartdegen et al. | 195/68 |
| 4,293,310 | 10/1981 | Weber | 23/230 |
| 4,414,323 | 11/1983 | Masuda | 435/7 |
| 4,414,325 | 11/1983 | Masuda et al. | 435/7 |
| 4,728,882 | 3/1988 | Stanbro et al. | 204/400 |
| 4,769,121 | 9/1988 | Newman | 5/06 |
| 4,786,600 | 11/1988 | Kramer et al. | 435/235 |
| 4,822,566 | 4/1989 | Newman | 436/806 |
| 4,935,207 | 6/1990 | Stanbro et al. | 436/806 |
| 4,938,742 | 7/1990 | Smits | 604/67 |
| 4,963,245 | 10/1990 | Weetall | 204/403 |
| 5,001,051 | 3/1991 | Miller et al. | 435/6 |
| 5,063,081 | 11/1991 | Cozzette et al. | 204/403 |
| 5,064,754 | 11/1991 | Mills | 435/6 |
| 5,071,733 | 12/1991 | Uekita et al. | 430/326 |
| 5,082,627 | 1/1992 | Stanbro | 204/403 |
| 5,164,319 | 11/1992 | Hafeman et al. | 204/400 |
| 5,187,096 | 2/1993 | Giaever et al. | 435/291 |
| 5,194,133 | 3/1993 | Clark et al. | 204/403 |

FOREIGN PATENT DOCUMENTS

| | | | |
|---|---|---|---|
| 0347579 | 5/1989 | European Pat. Off. | |
| 0402917 | 12/1990 | European Pat. Off. | 33/48 |
| 3801987 | 7/1989 | Germany. | |
| 2202045 | 9/1988 | United Kingdom. | |
| 8808528 | 11/1988 | WIPO. | |
| 8809499 | 12/1988 | WIPO. | |
| 8910977 | 11/1989 | WIPO. | |
| 9002327 | 3/1990 | WIPO | 33/545 |
| 9003382 | 4/1990 | WIPO | C07H 21/00 |
| 9005300 | 5/1990 | WIPO | 27/48 |
| 9015070 | 12/1990 | WIPO | C07K 1/04 |

OTHER PUBLICATIONS

"A Method for DNA Sequencing by Hybridization With Oligonucleotide Matrix", DNA Sequence—J. DNA Sequencing and Mapping, vol. 1, 1991, pp. 375–388.

"Genetic Analysis of Amplified DNA with Immobilized Sequence–Specific Oligonucleotide Probes", Proc. Natl. Acad. Sci. USA, vol. 86, Aug. 1989, pp. 6230–6234.

"Use of Thiol–Terminal Silanes and Heterobifunctional (List continued on next page.)

Primary Examiner—James C. Housel
Assistant Examiner—Christopher L. Chin
Attorney, Agent, or Firm—Vinson & Elkins

[57] ABSTRACT

A method and apparatus for identifying molecular structures within a sample substance using an array having a plurality of test sites upon which the sample substance is applied. Each test site includes a probe formed therein to bond with an associated target molecular structure. An electrical signal is applied to the test site and the electrical properties of the test sites are detected to determine which probes have bonded to an associated target molecular structure.

30 Claims, 2 Drawing Sheets

OTHER PUBLICATIONS

Crosslinkers for Immobilization of Antibodies on Silica Surfaces", Analytical Biochemistry 178, 1989, pp. 408–413.

"Immobilization of Acetylcholinesterase on Solid Surfaces;Chemistry and Activity Studies", Sensors and Actuators, B. 3, 1991, pp. 311–337.

"Covalent Immobilization of DNA onto Polystyrene Microwells: The Molecules Are Only Bound at the 5'End", Analytical Biochemistry 198, 1991, pp. 138–142.

"A Sub–Micron Particle Filter in Silicon", Sensors and Actuators, A21–A23, 1990, pp. 904–907.

"Dielectric Dispersion of DNA", by Shiro Takashima, Journal of Molecular Biol., Feb. 13, 1963, 7 pp. 455–467.

"A 1024–Element High–Performance Silicon Tactile Imager", Suzuki et al., IEDM 88 1983 IEEE, pp. 674–677.

"Micro–Diaphragm Pressure Sensor", Sugiyama et al., IEDM 86, 1986 IEEE, pp. 184–187.

"Silicon Pressure Sensor Based on a Resonating Element", Buser et al, Sensors and Actuators A, 25–27 (1991) Elsevier Sequoia, The Netherlands, pp. 717–722.

"Q–Factor and Frequency Shift of Resonating Silicon Diaphragms in Air", Prak et al., Sensors and Actuators A, (1991) Elsevier Sequoia/The Netherlands, pp. 691–698.

"A Digital Optically Multiplexed Charge Coupled Device (CCD) Based Deoxyribonucleic Acid (DNA) Sequence Header", Craine et al., SPIE, vol. 914 Medical Imaging II, (1988).

"Biotinyl and Phosphotyrosinyl Phosphoramidite Derivatives Useful in the Incorporation of Multiple Reporter Groups on Synthetic Oligonucleotides" Misiura et al, 1990 Oxford University Press, Nucleic Acids Research, vo. 18, No. 15, pp. 4345–4354.

*Sensitive Detection Systems,* "Chemiluminescent and Bioluminescent Techniques", L. J. Kricka, Clin. Chem. 37/9, (1991) pp. 1472–1481.

"Nonradioactive Nucleic Acid Detection by Enhanced Chemiluminescences Using Probes Directly Labeled with Horseradish Peroxidase", Pollard–Knight et al., *Analytical Biochemistry* 195 (1990), pp. 84–89.

"Multiwavelenght Fluorescence Detectino for DNA Sequencing Using Capillary Electrophoresis", Oxford University Press, Nucleic Acids Research, vol. 19, No. 18, pp. 4955–4962.

"Imaging of Fluorescent and Chemiluminescent DNA Hybrids Using a 2–D CCD Camera", Karger et al., SPIE vol. 1206, New Technologies in Cytometry and Molecular Biology (1990), pp. 78–89.

Product Review, Nature, vol. 329 (Oct. 8, 1987) "Biosensors emerge from the laboratory", J. Briggs, pp. 565.

"Sub–Femtomole Quantitation of Proteins with Threshold®, for the Biopharmaceutical Industry", Briggs et al., *BioTechniques,* vol. 9, No. 5 (1990) pp. 1–8.

"A Swept–Frequency Magnitude Method for the Dielectric Characterization of Chemical and Biological Systems", Hollis et al., Jul. 1980 *IEEE Transactions And Microwave Theory And Techiques,* vol. MTT–28, No. 7, pp. 791–801.

"Two–Dimensional Spatial Light Modulators: A Tutorial", Neff et al., IEEE, vol. 78, No. 5.

"Deformable–Mirror Spatial Light Modulators", Hornbeck et al., SPIE Critical Reviews Series vol. 1150, p. 86.

A proposal sent by Houston Advanced Research Center (HARC) to the National Institutes of Health in Jul. 1991. This Material describes the overall background and approaches for the fabrication of geo–sensors that were envisioned by HARC at that time.

Halliday et al, *Physics,* New York, John Wiley & Sons, 1978, p. 658.

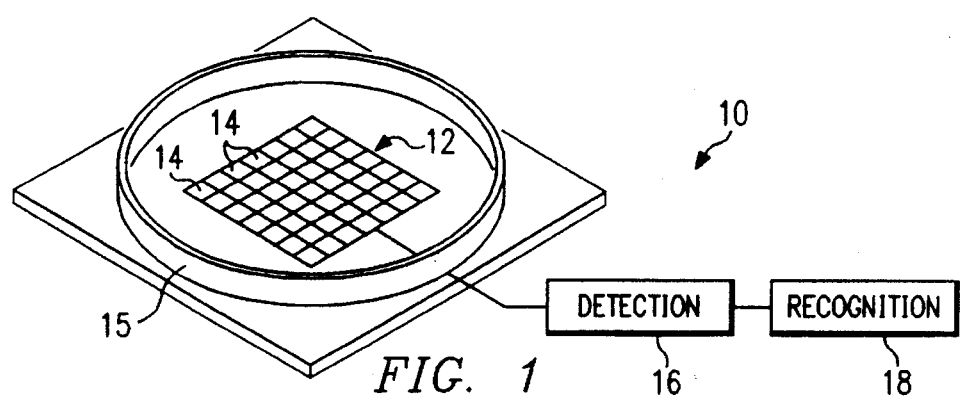
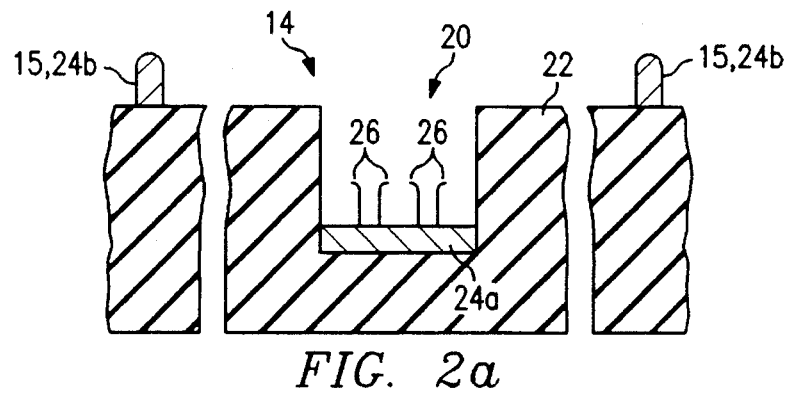
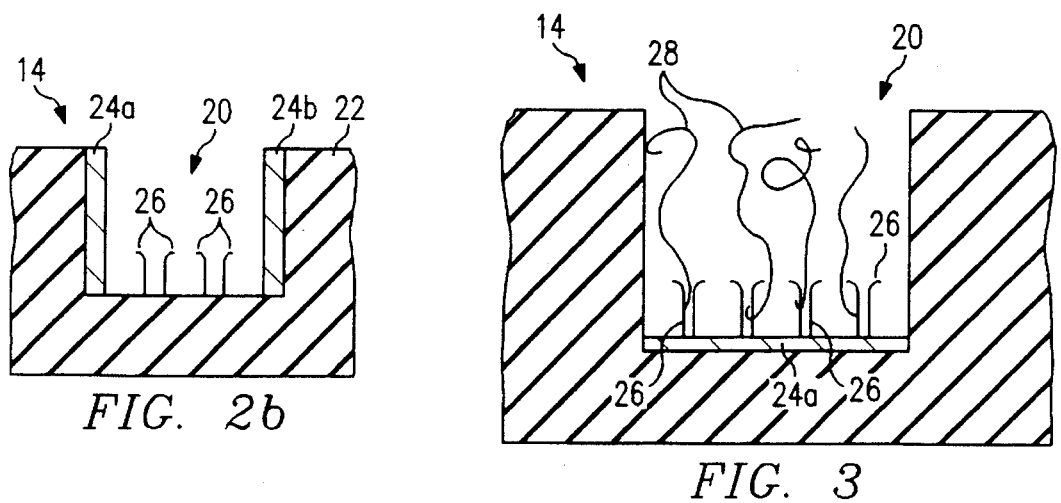

MULTI-SITE DETECTION APPARATUS

RELATED APPLICATIONS

This application is a continuation of application Ser. No. 07/794,036, filed Nov. 19, 1991, and entitled "Method and Apparatus for Molecule Detection", now abandoned.

TECHNICAL FIELD OF THE INVENTION

This invention relates in general to molecule detection, and more particularly to a method and apparatus of determining the presence of bound molecules at specific spatial locations in an array.

BACKGROUND OF THE INVENTION

In many applications, it is desirable to detect the presence of one or more molecular structures in a sample. For example, a DNA or RNA sequence analysis is very useful in genetic and disease diagnosis, toxicology testing, genetic research, agriculture and pharmaceutical development. Likewise, cell and antibody detection is important in disease diagnosis.

A number of techniques have been developed for molecular structure detection. In DNA and RNA sequence detection, two procedures are generally used, autoradiography and optical detection. Autoradiography is performed using $^{32}P$ or $^{35}S$. For DNA sequence analysis applications, nucleic acid fragments are end labeled with $^{32}P$. These end labeled fragments are separated by sizes, then exposed to x-ray film for a specified amount of time. The amount of film exposure is related directly to the amount of radioactivity adjacent to a region of film.

The use of any radioactive label is associated with several disadvantages. First, prolonged exposure to radioactive elements increases the risk of acquiring genetic diseases, such as cancer. As such, precautions must be implemented when using radioactive markers or labels to reduce the exposure to radioactivity. Typically, workers must wear a device to continually monitor radioactive exposure. In addition, pregnant females should take additional precautions to prevent the occurrence of genetic mutations in the unborn.

Further, the incorporation of a radioactive label into a nucleic sequence increases the complexity and cost of the entire sequence analysis process. Although the chemistry is commonplace, it nonetheless necessitates an additional step. The film exposure also increases the required labor and cost of materials. The increase in cost is due to the extra reagents necessary for end labelling, as well as precautionary steps necessary for the safe handling of radioactive materials.

The radioactive detection scheme has sensitivity limitations in both the temporal and spatial domains. The use of radioactive labelling currently has a spatial resolution of one millimeter. Additional hardware and software are required to reduce the spatial resolution below one millimeter. The sensitivity of detection of the autoradiographic film is related directly to the amount of time during which the radioactive labelled fragments are exposed to the film. Thus, the exposure time of the film may range from hours to days, depending upon the level of radioactivity within each detection test site. A β scanner may drastically reduce the time required for film exposure during radiography. However, the use of the β scanner significantly increases the expense associated with this type of detection, and has intrinsically poor spatial resolution.

Optical detection of fluorescent labelled receptors has also been utilized to detect molecular binding. Briefly, for DNA sequence analysis applications, a base-specific fluorescent dye is attached covalently to the oligonucleotide primers or to the chain terminating dideoxynucleotides. The appropriate absorption wavelength for each dye is chosen and used to excite the dye. If the absorption spectra of the dyes are close to each other, a specific wavelength can be chosen to excite the entire set of dyes.

A separate optical detection technique involves the use of a dye, for example, ethidium bromide, which stains duplexed nucleic acids. The fluorescence of these dyes exhibits an approximate 20-fold increase when it is bound to duplexed DNA or RNA, when compared to the fluorescence exhibited by unbound dye, or dye bound to single-stranded DNA. This type of dye is used to detect the presence of hybridized DNA (or RNA) during a hybridization experiment. Although the use of optical detection methods increases the throughput of the sequencing experiments, the disadvantages are serious.

The various dyes employed in using fluorescent labelled molecules have been shown to be mutagenic and, hence, carcinogenic. For example, ethidium bromide can intercalate into human DNA, and during replication, specific regions of DNA may not be replicated exactly. Proper precautions, such as gloves and careful experimental techniques, can provide the worker with protection against dye penetration. However, it is advantageous to reduce the exposure to these mutagenic agents. In addition, pregnant females should take extra precautions to prevent the occurrence of genetic mutations in the unborn.

Incorporation of a fluorescent label into a nucleic acid sequence increases the complexity and cost of the entire process. Although the chemistry is commonplace, it necessitates an additional step. The increase in cost is due to the extra reagents necessary for fluorescent labeling, as well as precautionary steps necessary for safe handling of mutagenic materials.

Furthermore, the use of multiple fluorescent dyes may affect the electrophoretic mobility of the labelled molecules. Scientists have found that a mobility correction factor is required for the sequence data because the fluorescent dyes influence the electrophoretic mobility of the nucleic fragments to which they are bound. The use of an optical detection method almost always necessitates the use of a laser with one or more lines. Extra precautions, depending upon the chosen wavelength, must be taken to ensure safe operation of the laser. Depending upon the required output power, this investment may range from a few hundred to many thousands of dollars.

Aside from the laser, additional hardware must be purchased for the operation of a fluorescent-based system. For example, a fluorescent detector and optics which transmit the fluorescent data to the detector are necessary elements of this system. If multiple excitation emission wavelengths are chosen, then a control system must be included to select the proper wavelength associated with a particular dye. Additionally, the fluorescent dyes must be purchased from a vendor.

Therefore, a need has arisen in the industry for a safe, low-cost, fast and accurate method and apparatus for detecting molecular structures at reduced complexity.

SUMMARY OF THE INVENTION

In accordance with the present invention, a method and apparatus for operable to simultaneously detect multiple molecular structures is provided which substantially eliminates or prevents the disadvantages and problems associated with prior devices.

In the present invention, a substance is applied to a plurality of test sites, each test site having a probe formed therein capable of binding to a known molecular structure. Electrical signals are collectively applied to the test sites, and electrical properties of the test sites are detected to determine whether the probe has bonded to an associated molecular structure.

The present invention provides significant advantages over the prior art. First, the exposure to radioactive elements, mutagenic fluorescent dyes, or other dangerous materials is eliminated. Second, the use of the present invention greatly reduces time and materials, because the sample substance is simply added to the test sites and allowed to bind using a minimal sample and minimal test reagents. The training time to instruct workers on use of the present invention is minimal. Additionally, the sensitivity limit can be reduced to the dimensions of the microfabricated test site which is estimated to be as small as one square micrometer. The present invention has been shown to provide a factor of ten in discrimination between bonded and non-bonded single-stranded DNA fragments, wherein the intercalating dye optical approach provides only a factor of three.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 illustrates a schematic representation of a detection/sequencing apparatus;

FIGS. 2a–b illustrate exemplary test wells for use in the array of FIG. 1;

FIG. 3 illustrates bonding of targets to probes within a test site;

DETAILED DESCRIPTION OF THE INVENTION

Figure 4:
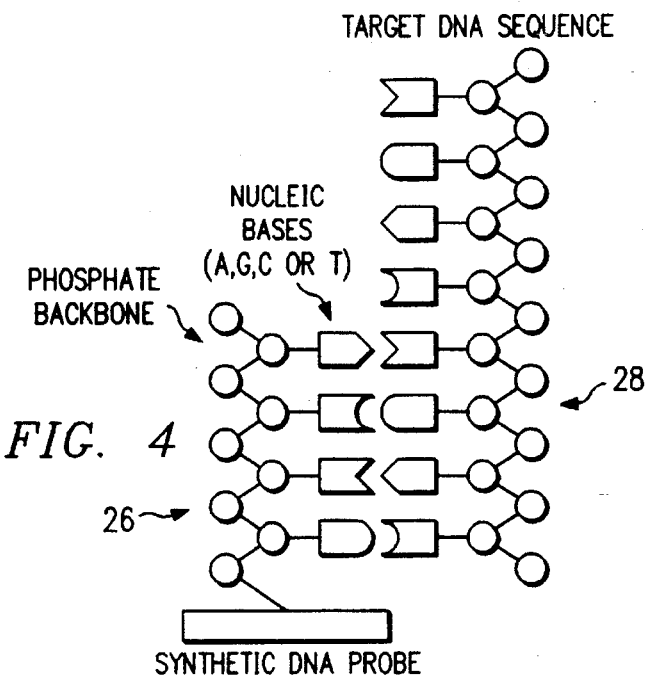
FIG. 4 illustrates bonding of a synthetic DNA probe to a target DNA sequence.

The preferred embodiment of the present invention and its advantages are best understood by referring to FIGS. 1–7 of the drawings, like numerals being used for like and corresponding parts of the various drawings.

FIG. 1 illustrates a preferred embodiment of the present invention used in connection with RNA and DNA sequencing. As described hereinbelow, the present invention may also be used for cell detection and antibody detection.

The sequencer 10 comprises an array 12 of test sites 14 surrounded by ring 15, detection circuitry 16 and recognition circuitry 18. In the preferred embodiment, array 12, detection circuitry 16 and recognition circuitry 18 are implemented as a single integrated circuit.

In operation, the test sites 14, described in greater detail hereinbelow, are formed in a semiconductor wafer using standard photolithographic techniques. Each test site contains a plurality of probes, which are capable of binding to known molecular structures (hereinafter "target"). The targets could comprise, for example, biopolymers, such as polynucleotides, DNA, RNA, cells, or antibodies. For the case of a RNA and DNA sequencer, the synthetic probes may comprise, for example, oligonucleotides. Different probes are used in test sites 14 for simultaneous detection of a plurality of different targets within a single array 12.

When a sample substance containing the targets in an electrolytic solution is poured into ring 15, the targets bind with associated probes within test sites 14. After sufficient time for binding, the surface is rinsed to remove excess targets or other unbound molecular structures. The remaining target structures will be, for the most part, bound to the probes attached to the microfabricated array 12 at specific test sites 14. Each test site 14 is subsequently interrogated electronically by the detection circuitry 16 to determine whether targets have bound in that test site. The detection circuitry 16 may be either on-chip or off-chip. Each test site 14 is then addressed by the detection circuitry 16. Test sites having bound targets will have changed electrical parameters, which may be detected. Thus by electronic addressing, the detection of specific target/probe bindings is achieved at each test site 14 within the microfabricated array 12, thereby determining the composition of the targets that are present within the sample substance.

The recognition circuitry 18 is specific to the DNA sequencing. The recognition circuitry 18 performs a sequence analysis (described below) based on the composition of the targets (nucleic acids) detected by the detection circuitry 16. Other circuitry for processing information related to target detection may be provided for other applications.

Test Sites

Exemplary test sites 14 are shown in FIGS. 2a–b. Many such test sites would be formed on a single substrate to simultaneously detect a plurality of targets. In FIG. 2a, a well 20 is formed in a layer of insulating material 22, such as silicon dioxide. A first plate 24a that serves as an capacitor plate is formed at the bottom of the well. In this embodiment, ring 15 is formed from a conductive material, and acts as second plate 24b of a capacitor. Probes 26 are formed on electrode plate 24a.

FIG. 2b illustrates a similar structure. Again, a well 20 is formed in an insulating layer 22. First and second plates 24a and 24b are formed on two sides of the well to serve as a localized electrode pair. Probes 26 are attached to the bottom of the well.

In use, targets from the sample substance bind to the probes 26 in the respective test sites 14. As the targets 28 bind to the probes 26 (see FIG. 3), the dielectric properties associated with the well 20 will change. The structure of FIG. 2a forms a capacitor between the plate 24a and a ring 15 (second plate 24b) 24b. Similarly, the test site 14 of FIG. 2b forms a parallel plate capacitor between plates 24a and 24b. The material under test acts as the dielectric located between the two plates.

Changes in the dielectric properties of the capacitors formed by the test sites 14 of FIGS. 2a–b are detected by detection circuitry 16 after binding of the sample substance. For illustration, a specific embodiment of the detection method and device is discussed in detail for detecting hybridized DNA for DNA sequence analysis. In this application, the device detects the binding of target DNA to known oligonucleotide probes 26 placed strategically on a microfabricated substrate, such as those shown in FIGS. 2a–b. The bonding mechanism is shown in FIG. 4.

DNA/RNA Sequencing Processing

Subsequent processing of the pattern of target DNA/probe binding can be used to determine the linear sequence of nucleic bases.

Table I shows an exemplary list of 8-base synthetic oligonucleotide probes for which binding might be detected responsive to a target single strand (16 base) DNA molecule. The array would contain all possible 8-base probes. The nine detected 8-base probes are correlated by recognition circuitry performs an overlapping algorithm to arrange the 8-base sequences as shown in Table II. The DNA target can thus be determined to be 3'-ATCGCTTACGGTAATG-5' by taking the complement of the resultant 16-base overlapping sequence.

TABLE I

Detected 8-Base Synthetic Oligonucleotide Probes
(Alphabetical Order 5' → 3')

AATGCCAT
AGCGAATG
ATGCCATT
CGAATGCC
GAATGCCA
GCCATTAC
GCGAATGC
TAGCGAAT
TGCCATTA

TABLE II

Overlapping Sequences of 8-Base Probes

5'-TAGCGAAT
　AGCGAATG
　　GCGAATGC
　　　CGAATGCC
　　　　GAATGCCA
　　　　　AATGCCAT
　　　　　　ATGCCATT
　　　　　　　TGCCATTA
　　　　　　　　GCCATTAG-3'
5'-TAGCGAATGCCATTAG-3'

Detection

Detecting the presence of target DNA in the test site 14 on the array 12 is simply a binary decision—whether or not the target DNA 28 has bound to a particular DNA probe 26. The DNA target is substantially longer than the synthetic probe 26 (for example, a 100 base target DNA compared to an 8 base probe). Therefore, as a result of the binding, the physical properties of the test site 14 changes because of the increased DNA mass and the reorientation of counter-ions in the solution.

The detection circuitry 16 can rapidly detect a change in the local electrical properties at each test site 14 likely caused by counter-ion reorientation. Traditionally, electrical properties of materials in the frequency range from DC to MHz have been characterized by conductance $\sigma$ (ease in which collective charge carriers can be moved under the influence of an electric field) and permittivity $\epsilon$ (amount in which localized charge distributions can be reoriented under the influence of an electric field). For materials with low conductance, such as dielectrics, characterization is primarily made by measuring the dielectric constant, or equivalently, relative permittivity $\epsilon$. The dielectric constant is independent of the sample size, and hence, serves as a characteristic material property. However, the dielectric constant often exhibits a frequency dependent effect—dielectric dispersion—due to the progressive inability of the local dipole charge distributions to reorient themselves with an applied alternating electric field of increasing frequency. As a consequence, the specific polarization of the material "relaxes" at a frequency $f_r$, resulting in a decreased dielectric constant. This relaxation frequency is related to the relaxation time $\tau = 1/2\pi f_r$ which is the time required for $e^{-1}$ of the dipoles to align themselves to an instantaneously applied electric field. The permittivity may be expressed as a frequency dependent complex number (see Debye, P., *Polar Molecules,* The Chemical Catalog Co., New York, (1929)), which is incorporated by reference herein:

$$\bar{\epsilon}(\omega) = \epsilon_\infty + (\Delta\epsilon/(1+j\omega\tau))$$

where $\epsilon_\infty$ is the relative permittivity measured at a significantly high frequency at which no polarization occurs, and $\Delta\epsilon = \epsilon_S - \epsilon_{107}$, where $\epsilon_S$ is the static (DC) relative premittivity. Alternatively, the permittivity can be expressed in real and imaginary form as:

$$\begin{aligned}\epsilon(\omega) &= \epsilon_{\infty +}(\Delta\epsilon(1-j\omega\tau)/(1+\omega^2\tau^2) \\ &= (\epsilon_\infty + (\Delta\epsilon/(1+\omega^2\tau^2))) - j(\Delta\epsilon\omega\tau/(1+\omega^2\tau^2)) \\ &= \epsilon' - j\epsilon''\end{aligned}$$

where $\epsilon'$ represents energy storage (lossless exchange of energy between electric field and sample) and $\epsilon''$ represents energy loss (energy lost from electric field and absorbed in the material usually in the form of heat). Also a dissipation factor $$D = \epsilon''/\epsilon'$$

can be defined representing the relative dissipation or absorption properties of the material. Several measurement techniques are available for obtaining these desired dielectric values (see von Hippel, A., *Dielectrics and Waves,* Wiley, New York (1954), which is incorporated by reference herein). Most measurement techniques involve constructing a relatively large test fixture that resembles a parallel plate capacitor. The material under test is sandwiched between two electrode plates, each of area A and separated by a distance d. With $d << \sqrt{A}$, a near uniform electric field is produced through the material with low fringe field effects, and subsequent capacitance measurements yield the real part of the complex permittivity $$\epsilon' = (Cd)/(A\epsilon_o).$$

The imaginary part can be obtained by measuring the dissipation factor D.

Utilizing a four-terminal parallel plate test fixture, the electrical properties of DNA in a low concentration aqueous solution can be obtained. Four-terminal fixtures are typically used in dielectric measurements to minimize unwanted residual factors arising from self and/or mutual induction between the leads. Graphs of DNA dielectric dispersion represented by $\epsilon'$ and $\epsilon''$ are well known and are described in greater detail in Takashima, S., J. Mol. Biol. 7:455–467 (1963), which is incorporated by reference herein. The dispersion arises from the negatively charged phosphate groups assembled in the backbone of the DNA molecule which attract the counter-ions in the solution. Although the DNA has no helix dipole moment (since it is a simple linear polyphosphate), a large dipole is induced from the counter ions in the solution being reoriented along the DNA backbone under the influence of an applied electric field. The dispersion, and hence relaxation frequency, is dependent upon the ion mobility, permittivity of the surrounding ionic medium, and the length of the DNA according to $$f_r = (2\mu z q^2 / \pi \epsilon) / L^2$$

where:

L is the effective molecular length of the DNA, q is the electron charge, $\mu$ is the counter-ion surface mobility, z is the number of ions in the surrounding ionic solution, and $\epsilon$ is the effective permittivity of the surrounding ionic solution of z ions.

Thus, a factor of 10 change in effective DNA base length representing the variation from a nonhybridized state (10 mer DNA probe) to a hybridized state (10 mer DNA probe hybridized with a 100 base single-stranded DNA target molecule) corresponds to a factor of 100 change in relaxation frequency. Thus, the dielectric relaxation frequency obtained through dielectric measurements is a distinguishable detection mechanism for hybridization.

The limitation to applying conventional relaxation measurement approaches to hybridization detection is the requirement of a relatively large parallel plate test fixture for each probe site. Coupled with the relatively long time (seconds) required for recording the measurements and extracting the relaxation frequency, use of conventional large plate test fixtures is impractical for DNA sequence analysis applications.

The microfabricated device and detection technique disclosed enables fast detection of hybridization for large DNA probe arrays. Essentially micro-sized dielectric test fixtures as shown in FIGS. 2a–b, are embedded in a conventional microelectronic substrate using standard photolithography etching techniques. In FIG. 2a, a suitable microelectrode forms the base of the test fixture with an approximate area of 100 μm². Synthetic oligonucleotide probes 26 are attached to the base microelectrode. As the longer DNA ligand 28 is washed onto the surface, hybridization will occur in only those miniature test sites 14 on the chip which contain complementary DNA probe molecules. The resulting wells containing bound DNA exhibit different electrical properties, hence providing the detection mechanism.

Figure 5:
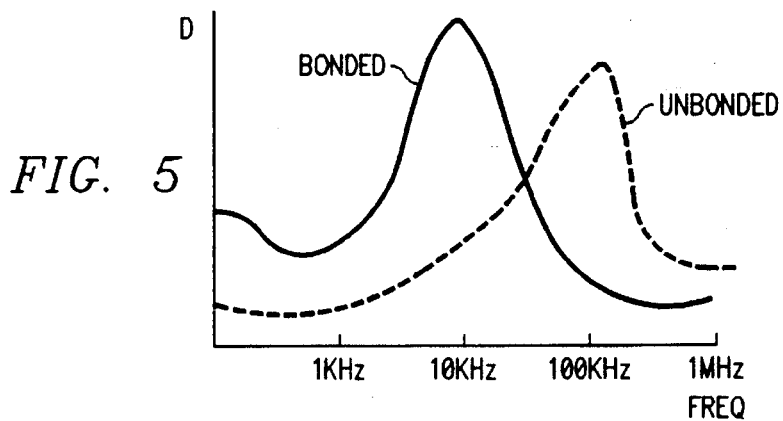
FIG. 5 illustrates a graph of dispersion as a function of frequency representative of bonded and unbonded test sites.

By applying a signal of varying frequency to each of the test sites, the relaxation frequency of the test site can be determined. The resultant relaxation frequency will indicate whether or not bonding has occurred within the test site. An exemplary graph of dispersion as a function of frequency representation of bonded and unbonded test sites is shown in FIG. 5. Whether a test site is bonded or unbonded can be determined either by scanning a range of frequencies to determine the relaxation frequency or by applying discrete frequencies to the test site and comparing the dispersion (D) at each frequency. At a minimum, two frequencies must be applied, the expected relaxation frequency of an unbonded test site and the expected relaxation frequency of a bonded test site.

Probes

One method of forming the array 12 uses probes attached to the test sites 14 in a test array 12. Different probes can be attached to the test sites 14 according to the type of target desired, including the use of oligonucleotides, single or double stranded DNA or RNA, antibodies or antigen-antibody complexes, tumor cells and other test probes known to those of skill in the art. The probes are attached to the test sites by fixation to a solid support substrate on the surface of the wells 20, or alternatively, attached directly to the plates. For example, the probes could be attached directly to plate 24a of FIG. 2a or to plates 24a–b of FIG. 2b. The solid support substrates which can be used on the surface of the wells 20 include inorganic substrates such as glass, polystyrenes, silicon dioxide, and silicon nitrate. The solid support substrates must be functionalized to create a surface chemistry conducive to the formation of covalent linkages with the selected probes. As an example, a glass support can be functionalized with an epoxide group by reaction with an epoxy silane. The epoxide group on the support reacts with a 5'-amino-derivatized oligonucleotide probe to form a secondary amine linkage, as described in Parkam and Loudon, BBRC 1:1–6 (1978), which is incorporated by reference herein. Formation of this covalent linkage attaches the probes 26 to the support surface in the desired array. Examples of functionalized polystyrene surfaces include 5" aldehyde or carboxylic acid derivatives coupled to hydrazide-activated polystyrene as described in Kremsky, et al. (1987) Nucl. Acids Res. 15:2891–2909, and 5' amino derivatives coupled to polystyrene which has been activated by diazotization and 5' phosphate derivatives coupled to amino-functionalized polystyrene as describe in Lund, et al. (1988) Nucl. Acids Res. 16:10861–10880, both articles being incorporated by reference herein.

For direct attachment of probes to the plates 24a–b, the plate surface must be fabricated with materials capable of forming conjugates with the probes. Materials which can be incorporated into the surface of the plates to provide for direct attachment of probes include electrometal materials such as gold, niobium oxide, iridium oxide, platinum, titanium and other metals. These electrometals are capable of forming stable conjugates directly on the plate surface by linkages with organic thiol groups incorporated into the probe as described in Whitesides, et al. (1990) Langmiur 6:87–96 and Hickman, et al. (1991) J. Am. Chem. Soc. 113:1128–1132, both of which are incorporated by reference herein. As an example, a synthetic DNA probe labeled with a thiol group at either the 5' or 3' end will form a stable conjugate with a metal such as gold in the plate surface to create an array of directly attached probes.

In preliminary work, functionalized solid support substrates were prepared by incorporating an epoxide-amine chemistry onto a glass solid support followed by coupling to oligonucleotide probes with a primary amine at the 5' terminus ($NH_2$-$(CH_2)_6$). Glass plates are cleaned by soaking in concentrated nitric acid, followed by rinsing with water and ethanol, then baking at 150° C. for several hours. Plates are rinsed thoroughly with chloroform and acetonitrile and stored under vacuum in a desiccator. The surface is then uniformly silanized by treatment with 10% dichloridi-methylsilane in toluene overnight, followed by rinsing with methanol. An array of wells (1 mm in diameter and 0.25 mm deep) is then drilled into the surface to expose fresh nonsilanized glass. Wells are cleaned with nitric acid, followed by rinsing with water and ethanol and baking at 80° C. overnight. The glass surface of the wells is then derivatized with gammaglycidoxypropyltrimethoxysilane (epoxysilane). Among the solvent systems investigated, a 90% epoxysilane containing 10% diisopropyl-ethylamine appeared to give the highest density of active epoxide.

Another method of forming the array involves fabricating the probes on the substrate, which may be better suited for larger arrays. On-chip synthesis of probes is described in PCT International Publication Number WO 90/15070, entitled "Very Large Scale Immobilized Peptide Synthesis" to Pirrung et al., assigned to Affymax Technologies, having an International Publication Date of Dec. 13, 1990, which is incorporated by reference herein.

Applications

Commercial applications of the present invention with regard to DNA and RNA detection include genetic research, genetic and infectious disease diagnosis, toxicology testing, individual identification, agriculture identification and breed optimization, quality assurance through contaminant detection, and occupational hazard screening via mutation detection.

There are currently estimated to be 4,000 to 5,000 genetic diseases in humans, in which a mutational change in a gene destroys or hinders the function of a gene product, leading to a serious medical condition. The affected genes and proteins (gene products) have thus far been identified for a small fraction of human genetic diseases, although the number is increasing steadily. A few examples of human genetic diseases for which mutations associated with the disease have been identified include cystic fibrosis, phenylketonuria, Alzheimers' disease, cancer, Duchenne muscular dystrophy, and familial hypercholesterolemia. Although, in some cases, the disease is associated with one or very few specific mutations, it is becoming evident that many, if not most genetic diseases can be caused by any of numerous mutations, scattered along the affected gene. In the former case, the presence of a defective gene can be detected through the use of simple DNA hybridization detection tests in which a synthetic DNA probe is used to discriminate between a wild type and mutant DNA sequence. In the latter case, a substantial DNA sequencing effort is required to search through an entire gene for mutations that may be associated with a disease.

The importance of detecting mutations within disease-linked genes lies in both the ability to screen for carriers of recessive genetic diseases, leading to genetic counseling and informed reproductive decisions, and the means for making prenatal diagnoses which can enable therapeutic intervention. By appropriate choice of oligonucleotide probes, the sequencer 10 leads to a new gene-targeted DNA sequencing procedure which rapidly detects any mutation within a target gene, facilitating the diagnosis of genetic diseases and identification of carriers, especially when a variety of different mutations may cause the defect. Perhaps even more important is the rapid, high throughput nature of the procedure which promises to facilitate population studies aimed at discovering which mutations within a target gene are actually associated with a disease and which mutations represent harmless polymorphisms. This information is expected to lead to simplification of the technology for specific detection of disruptive mutations, and valuable structure-function relationships that facilitate the development of therapeutics.

The present invention is not limited to genetic diseases; it may be used for rapid, high throughput identification of infectious agents. Each species or strain of a virus or micro-organism is predicted to yield a unique, diagnostic pattern of hybridization within an array 12.

The gene-targeted mutation detection described above will also have important uses in environmental research, for example, the detection of mutations induced by chronic exposure of cells to chemical agents. Similarly, the present invention may be used for individual monitoring of employees who may be exposed to chemicals or radiation in the workplace (e.g., through periodic screening for mutations in populations of circulating lymphocytes). An important application of this technology will be the development of a predictive model of mutagenic risk via the characterization of large scale and point mutations in specific genes, such as that for hypoxanthine-guanine phosphoribosyltransferase (HPRT).

High density arrays will find numerous uses in genome sequencing, and will likely play an important role in the current Human Genome Project (HGP) effort to determine the entire sequence of 3 billion base pairs in the human genome. More importantly, however, is the new human genome projects that will arise because of the availability of fast, high throughput sequencing technology. There will be a need to conduct repetitive DNA sequence analysis of important parts of the human genome derived from large numbers of individuals, in order to characterize complex multi-gene disease conditions and other genetic traits. This activity will persist long after the current HGP is completed and will bring revolutionary progress in biomedical sciences.

Another potential use of the present invention is in "DNA typing" in which DNA sequence differences between individuals are analyzed. The sequencer of the present invention for simultaneously screening large numbers of polymorphic markers in the DNA of an individual has tremendous advantages over the current technique of restriction fragment length polymorphism (RFLP) analysis, which is time consuming and laborious. DNA typing can play an important role in forensics and paternity testing. In addition, there is interest in DNA typing all personnel in the armed services.

As valuable new plants and livestock are developed by genetic engineering, there will be a need for DNA typing to verify the source and ownership of agricultural products. The sequence information that will come from genome sequencing in humans, plants and animals will lead to increased application of genetic engineering techniques to develop pharmaceutical agents and create improved crops and livestock. Examples include strains that are more resistant to disease and harsh climates, as well as crops that have a greater yield or higher nutritive value.

The present invention can be used in connection with detection of targets which are molecular structures other than DNA or RNA, such as cells and antibodies. Table III sets forth feasible probe types for other molecular structures serving as targets. The stated probe types are not meant to be exclusive.

TABLE III

| | Probe Types |
|---|---|
| Target | Probe |
| DNA, RNA | Oligonucleotide |
| Antibody | Antigen (peptide), anti-antibody |
| Cell | Antibody, protein |
| Hormone receptor | Hormone |
| Aviden | Biotin |
| Immunogobulin | Protein A |
| Enzyme | Enzyme Factor |
| Lectins | Specific Carbohydrate |

Figures 6, 7:
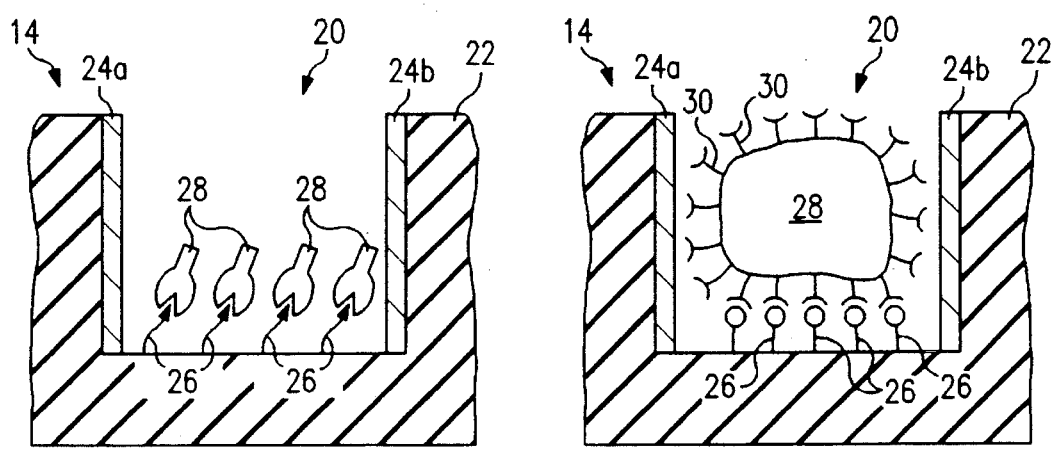
FIG. 6 illustrates a test well for detection of antibodies in a sample.
FIG. 7 illustrates a test site for detecting specific cell types in a sample.

When the detector employs peptides or other antigens as probes, it can be used to detect antibodies in biological fluids, as shown in FIG. 6.

In this embodiment, a peptide antigen (the probe 26) is affixed to the solid support, employing a bifunctional crosslinker such as one with a silane at one end and an epoxide or other peptide specific group at the other.

The treated surface is then incubated with a fluid containing antibody (the target 28). Because antibodies are large macromolecules (150,000 to 950,000 MW, depending on class), the resulting target/probe interaction is associated with a large change in dielectric relaxation process. The magnitude of the effect can be additionally amplified by treating the target/probe complex with a second antibody which is specific for the target antibody, thereby creating a very large complex.

The affinity and selectivity of antibody/antigen and antibody-antibody interaction are well known and are the basis for an existing class of biotechnology (ELISA assays, immunohistochemistry, and others). The technology described here employs those well understood binding interactions in a new microelectronic detection scheme.

The commercial application of the methodology is that it could be used to detect the presence of hundreds or thousands of different antibodies or other proteins, simultaneously, in a blood sample or other cellular fluid. This is particularly useful in blood typing, the detection of viral infection such as AIDS, or the diagnosis of cancer. It would also be very useful as a research tool. It would replace or augment the use of ELISA assays and other biochemical methods to detect antibody/antigen interaction.

When the detector employs as a probe, peptides, antibodies or other molecules which bind to cells, it can be used to detect specific cell types in biological fluids as shown in FIG. 7.

In this embodiment, the probe 26 comprises an antibody, protein or other molecule which is known to bind to the cell surface. The target 28 in this case is an intact cell having receptors 30 for bonding with the probes 26.

A fluid solution containing cells is added to the detector. Subsequent to the target/probe binding interaction, binding gives rise to detector wells which are coupled to a cell. Since cells do not conduct current and display low frequency dielectric relaxation, binding of a cell can be detected by either a change in absolute conduction in a well (a modification of the Coulter principle) or by the induction of a low frequency dielectric relaxation effect.

The commercial application of the methodology is that it could be used to detect the presence of cells with altered cell surface properties, especially cells in the blood or other bodily fluids. Cells from solid tissues could be analyzed subsequent to standard tissue dispersement methods. Such a detector would be useful in the diagnosis of viral infection and for cancer diagnosis, as well as a scientific research tool. It would serve as a replacement for the use of fluorescence microscopy (immunohistochemistry) and fluorescence activated cell sorting.

Current microfabrication techniques enable inexpensive construction of multimegabit memories that exhibit uniform densities and properties. Hence arrays containing potentially millions of individual biological test wells or sites can be miniaturized comparable to standard electronic devices at a similar cost. For example, a 1 cm×1 cm array could easily be fabricated containing one million biological test sites. Moreover, the uniform electrical properties of the devices fabricated in such manner enhance the detection sensitivity beyond many other approaches.

One important advantage of the microfabricated device described above is that the detection method provides direct detection of target/probe molecular binding. Hence no toxic fluorescent or radioactive marker need be attached to the targets or probes. Rather, only an electrical distribution differential must be experienced for detection. Such an electrical distribution differential naturally occurs for many targets/probes binding, such as DNA and RNA to an oligonucleotide. However, if the differential upon bonding is weak or nonexistent, a charged molecular marker can be attached to the target. Specifically for the DNA hybridization detection embodiment, the direct detection method involves measuring the dissipation factor for the target/probe complex at each of the test sites in the array. The dissipation factor is a frequency discriminant. That is, detection is observed by a change in frequency characteristics, as opposed to a change in magnitude characteristics which can be obscured in time as the microfabricated array is exposed to the corrosive biological solutions. Thus, the device may be cleaned and reused a number of times without affecting its accuracy. Although the method of detection will withstand some corrosion of the plates 24a–b, a passivation layer can be employed to coat the plates for even longer use.

Another advantage of the present invention is that the electronic circuitry used to interrogate the test sites to perform the detection measurements can be fabricated directly on the wafer containing the biological array. Switch matrices, signal processing circuitry, and energy sources could all be incorporated on the same chip to facilitate rapid detection across the array. Consequently, the incorporation of active circuitry on the wafer would also greatly reduce the cost of experimentation.

The present invention eliminates the most important problems associated with the prior art. First, the exposure to either radioactive elements or mutagenic fluorescent dyes is eliminated. As such, the amount of hazards to which workers are exposed is greatly reduced. Second, the incorporation of a radioactive or fluorescent label into a nucleic acid sequence is not required. Thus, the present invention reduces both the required time and materials. The sample solution containing potential targets is simply added to the known probes on the array and allowed to bind. Worker training time would be reduced since these detection devices could be used by workers with minimal training.

Third, the sensitivity limit is reduced to the dimensions of microfabricated test site 14 (which can be as small as 1 micrometer$^2$). The sensitivity limitation of radiographic film and the electrophoretic mobility of the fluorescent dyes is not an issue. Rather, the density of the probes 26 attached at the test site 14 directly determines the sensitivity. The microelectronic method has been shown to provide a factor of ten discrimination between short (nonhybridized) and long (hybridized) single-stranded DNA fragments, whereas the intercalating dye optical approach provides a factor of three.

Fourth, the elimination of radiographic film reduces the time required since film exposure is not required. Sample preparation time is reduced greatly since the nucleic acid fragments need not be labeled. The detection method is quick; the measurements can be performed as soon as sufficient molecular binding is completed. Furthermore, the measurement process can be automated via microprocessor control to provide a very fast method of accessing each test site in the array.

Fifth, the microelectronic technology incorporated into these types of detection devices will drastically reduce the price for such experimentation. Essentially, the efficient mass production techniques employed in making megabit memory chips and megapixel CCD imaging chips can be employed. The hardware necessary for radioactive labeled techniques (β scanner) or for the fluorescent-based techniques (laser, CCD camera, PMT, optics, etc.) is not required.

Although the present invention and its advantages have been described in detail, it should be understood that various changes, substitutions and alterations can be made herein without departing from the spirit and scope of the invention as defined by the appended claims.

What is claimed is:

1. Apparatus for identifying molecular structures within a sample substance, comprising:
   a plurality of test sites formed in a single substrate, said test sites having respective probes attached thereto which specifically bind to a target molecular structure, such that different test sites have probes which specifically bind to different target molecular structures;
   a plurality of electrodes associated with the test sites, each test site having at least one electrode attached thereto for electrical coupling with a second electrode, wherein the one electrode and the second electrode are disposed adjacent to said test sites to form a capacitor in conjunction with the sample substance;
   circuitry, coupled to said electrodes, for applying an electronic signal to the test sites at multiple frequencies; and
   circuitry for detecting one of a plurality of frequency dependent electrical properties of the test sites to determine which probes have bound to an associated target molecular structure by measuring a dielectric property over a range of frequencies, wherein the plurality of frequency dependent electrical properties comprises permittivity, a dielectric relaxation frequency, and a dispersion of the test sites.

2. The apparatus of claim 1 wherein one or more of said probes bind to a DNA molecule.

3. The apparatus of claim 2 wherein said one or more probes comprise oligonucleotide probes.

4. The apparatus of claim 1 wherein one or more of said probes bind to a RNA molecule.

5. The apparatus of claim 1 wherein one or more of said probes bind to a cell.

6. The apparatus of claim 5 wherein said one or more probes comprise antibody probes.

7. The apparatus of claim 1 wherein one or more of said probes bind to an antibody.

8. The apparatus of claim 7 wherein said one or more probes comprise anti-antibody probes.

9. The apparatus of claim 8 wherein said one or more probes comprise peptide probes.

10. The apparatus of claim 1 wherein said test sites comprise:
   a plurality of wells formed in the substrate, said wells defined by side and bottom walls;
   probes for binding with a desired molecular structure formed in each well;
   wherein said electrodes are disposed adjacent to said walls to form a capacitor in conjunction with the sample substance.

11. The apparatus of claim 10 wherein said capacitors each comprise a plate formed in each well which is capacitively coupled to a ground plate common to each well.

12. The apparatus of claim 11 wherein said capacitors each comprise first and second plates formed on the sidewalls of the wells.

13. The apparatus of claim 1 wherein said circuitry for applying an electronic signal comprises circuitry for applying a signal over a predetermined range of frequency.

14. The apparatus of claim 13 wherein said detecting circuitry comprises circuitry for measuring capacitance to determine said relaxation frequency within said range.

15. The apparatus of claim 14 wherein said detecting circuitry further comprises circuitry for comparing said relaxation frequency to a known frequency for a test site with unbound probes.

16. The apparatus of claim 1 wherein said circuitry for applying an electronic signal comprises circuitry for applying a signal at discrete predetermined frequencies at a selected test site.

17. The apparatus of claim 16 wherein said detecting circuitry comprises circuitry for measuring capacitance of the sample substance at said selected test site at each of said discrete predetermined frequencies to determine said dispersion at the predetermined frequencies and comparing the dispersion between said frequencies to determine whether binding with a target molecular structure has occurred at said selected test site.

18. The apparatus of claim 1 and further comprising circuitry for determining a structure based on the test sites having bonded probes.

19. The apparatus of claim 1 wherein said test sites are formed on a semiconductor surface.

20. An integrated circuit for identifying molecular structures within a sample substance, comprising:

a plurality of test sites formed in a single substrate;

a plurality of electrodes associated with the test sites, each test site having at least one electrode attached thereto for electrical coupling with a second electrode, wherein the one electrode and the second electrode are disposed adjacent to said test sites to form a capacitor in conjunction with the sample substance;

probes attached to respective test sites, said probes being of various structures in order to specifically bind with respective predetermined molecular structures; and circuitry, coupled to said electrodes, for measuring capacitive parameters at multiple frequencies detect one of a plurality of frequency dependent electrical properties of the test sites to determine whether the probes associated with the test sites have bound with the respective predetermined molecular structures, wherein the plurality of frequency dependent electrical properties of the test sites comprises permittivity a dielectric relaxation frequency, and a dispersion of the tests sites.

21. The integrated circuit of claim 20 and further comprising processing circuitry for processing information from said measuring circuitry.

22. The integrated circuit of claim 20 wherein each of said test sites comprise first and second conducting plates formed with a well, said probes being disposed between said conductive surfaces.

23. The integrated circuit of claim 22 wherein said first and second plates are parallel.

24. The integrated circuit of claim 22 wherein said measuring circuitry is operable to generate a signal over a range of frequencies to said plates of each of said test sites and measure capacitance responsive thereto to determine the dispersion over said range of frequencies.

25. The integrated circuit of claim 22 wherein said detecting circuitry is operable to generate a signal at discrete frequencies to said plates of each of said test sites and measure capacitance responsive thereto to determine dispersion at said discrete frequencies.

26. Apparatus for identifying molecular structures within a sample substance, comprising:

a plurality of test sites formed in a single substrate, said test sites having respective probes attached thereto which specifically bind to a target molecular structure, such that different test sites have probes which specifically bind to different target molecular structures;

a plurality of electrodes associated with the test sites, each test site having at least one electrode formed therein for electrical coupling with a second electrode, wherein the one electrode and the second electrode are disposed adjacent to said test sites to form a capacitor in conjunction with the sample substance;

circuitry, coupled to said electrodes, for applying an electronic signal to the test sites over a range of frequencies; and circuitry for detecting capacitive parameters of the test sites within said range of frequencies to determine a relaxation frequency and comparing said relaxation frequency to a known frequency for a test site with unbound probes to determine which probes have bound to an associated target molecular structure.

27. Apparatus for identifying molecular structures within a sample substance, comprising:

a plurality of test sites formed as respective wells in a single substrate, said test sites having respective probes attached to said wells to specifically bind to an associated target molecular structure, such that different test sites have probes which specifically bind to different target molecular structures;

a plurality of electrodes formed on sidewalls of said wells;

a ground plate common to each well for providing a capacitive coupling to said electrodes;

circuitry, coupled to said electrodes, for applying an electronic signal to the test sites over a range of frequencies; and circuitry for detecting one of a plurality of frequency dependent electrical properties of the test sites by measuring capacitive parameters and dissipation of the test sites at multiple frequencies to determine which probes have bonded to an associated target molecular structure, wherein the plurality of frequency dependent electrical properties comprises permittivity, a dielectric relaxation frequency, and a dispersion of the test sites, 28. Apparatus for identifying molecular structures within a sample substance, comprising:

a plurality of test sites formed in a single substrate, said test sites attached to respective probes which specifically bind to a target molecular structure, such that different test sites have probes which specifically bind to different target molecular structures;

a plurality of electrodes associated with the test sites, each test site having a least one electrode formed therein for electrical coupling with a second electrode, wherein the one electrode and the second electrode are disposed adjacent to said test sites to form a capacitor in conjunction with the sample substance;

circuitry, coupled to said electrodes, for applying an electronic signal to the test sites at multiple frequencies; and circuitry for detecting a frequency dependent capacitive property of the test sites by measuring capacitive parameters of the test sites at multiple frequencies to determine which probes have bound to an associated target molecular structure, wherein the frequency despondent capacitive property of the tests sites is permittivity.

29. An integrated circuit for identifying molecular structures within a sample substance, comprising:

a plurality of test sites formed in a single substrate;

a plurality of electrodes associated with the test sites, each test site having at least one electrode formed therein for electrical coupling with a second electrode, wherein the one electrode and the second electrode are disposed adjacent to said test sites to form a capacitor in conjunction with the sample substance;

probes attached to respective test sites, said probes being of various structures in order to specifically bind with respective predetermined molecular structures; and circuitry, coupled to said electrodes, for detecting a frequency dependent capacitive property of the test sites by measuring capacitive parameters at multiple frequencies to determine whether the probes associated with the test sites have bound with the respective predetermined molecular structures, wherein the frequency dependent capacitive property of the tests sites is a dielectric relaxation frequency of the test sites.

30. An integrated circuit for identifying molecular structures within a sample substance, comprising:

a plurality of test sites formed in a single substrate;

a plurality of electrodes associated with the test sites, each test site having at least one electrode formed therein for electrical coupling with a second electrode, wherein the one electrode and the second electrode are disposed adjacent to said test sites to form a capacitor in conjunction with the sample substance;

probes attached to respective test sites, said probes being of various structures in order to specifically bind with respective predetermined molecular structures; and circuitry, coupled to said electrodes, for detecting a frequency dependent capacitive property of the test sites by measuring capacitive parameters at multiple frequencies to determine whether the probes associated with the test sites have bound with the respective predetermined molecular structures, wherein the frequency dependent capacitive property of the tests sites is a dispersion of the test sites.

* * * * *

UNITED STATES PATENT AND TRADEMARK OFFICE
CERTIFICATE OF CORRECTION

PATENT NO. : 5,532,128
DATED : July 2, 1996
INVENTOR(S) : Mitchell D. Eggers, Michael E. Hogan, Kenneth L. Beattie, John Shumaker, Daniel J. Ehrlich and Mark Hollis It is certified that error appears in the above-indentified patent and that said Letters Patent is hereby corrected as shown below:

Col. 6, ln. 18, delete "$\Delta\epsilon=\epsilon_s-\epsilon_{107}$", insert --$\Delta\epsilon=\epsilon_s-\epsilon_{00}$--

Col. 8, ln. 17, delete "5''", insert --5'--.

Col. 15, ln. 27, between "frequencies" and "detect", insert --to--.

Col. 16, ln. 31, delete "sites,", insert --sites.--.

Col. 16, ln. 54, delete "despondent", insert --dependent--.

Signed and Sealed this

Eighth Day of April, 1997

BRUCE LEHMAN

*Attest:*

*Attesting Officer*    Commissioner of Patents and Trademarks

UNITED STATES PATENT AND TRADEMARK OFFICE
CERTIFICATE OF CORRECTION

PATENT NO. : 5,532,128
DATED : July 2, 1996
INVENTOR(S) : Mitchell D. Eggers, Michael E. Hogan, Kenneth L. Beattie, John Shumaker, Daniel J. Ehrlich and Mark Hollis It is certified that error appears in the above-indentified patent and that said Letters Patent is hereby corrected as shown below:

On the title page correct "[73] Assignee" as follows:

Houston Advanced Research Center, The Woodlands, Tex.; Massachusetts Institute of Technology, Cambridge, Mass.; The Baylor College of Medicine, Houston, Tex.

Col. 1, ln. 3, please insert --

NOTICE

This invention was made with government support under Contract Number F19628-90-C-0002 awarded by the Air Force. The government has certain rights in the invention.--.

Signed and Sealed this

Twenty-ninth Day of April, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

ATCGCTTACG GTAATG               16

( 2 ) INFORMATION FOR SEQ ID NO:2:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

TAGCGAATGC CATTAG               16